US00PP16187P2

(12) United States Plant Patent
Zary

(10) Patent No.: US PP16,187 P2
(45) Date of Patent: Jan. 3, 2006

(54) CLIMBER ROSE PLANT NAMED 'JACADYNA'

(50) Latin Name: *Rosa hybrida*
Varietal Denomination: JACadyna

(75) Inventor: Keith W. Zary, Somis, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/849,360

(22) Filed: May 18, 2004

(51) Int. Cl.
*A01H 5/00* (2006.01)

(52) U.S. Cl. ..... Plt./112
(58) Field of Classification Search ..... Plt./112, Plt./115
See application file for complete search history.

*Primary Examiner*—Anne Marie Grunberg
*Assistant Examiner*—June Hwu
(74) *Attorney, Agent, or Firm*—Klarquist Sparkman LLP

(57) ABSTRACT

Climber rose plant having a strong, vigorous climbing habit; glossy, disease resistant foliage; constant bloom during the growing season; large flower clusters; good bud form; and ability to grow vigorously on its own roots.

1 Drawing Sheet

Genus and species: *Rosa hybrida*.
Variety denomination: 'JACadyna'.

ORIGIN OF THE INVENTION

The present invention relates to a new and distinct variety of a climber rose plant named 'JACadyna' which was originated by me by crossing the variety 'JACsat' (Dynamite), U.S. Plant Pat. No. 8,741, with the variety 'JACclam' (America), U.S. Plant Pat. No. 3,682.

BACKGROUND OF THE INVENTION

The primary objective of this breeding was to produce a new rose variety having the vigor, climbing habit, large flower and bud form of the female parent combined with the climbing habit, clusters and constant bloom of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Strong, vigorous climbing habit.
2. Glossy, disease resistant foliage.
3. Constant bloom during the growing season.
4. Large flower clusters.
5. Good bud form.
6. Ability to grow vigorously on its own roots.

Asexual reproduction of this new variety by cuttings, as performed at Wasco, Calif., shows that the foregoing and all other characteristics and distinctions come true to form and are established and transmitted through succeeding propagations.

Comparison with Parents

The subject variety differs from the bright red female parent in flower color, production of larger clusters and faster repeat bloom. It differs from the salmon colored male parent in flower color.

Comparison with Similar Variety

The subject variety most closely resembles the male parent 'JACclam' (America) but differs in flower color.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'JACsat' (Dynamite).
*Pollen parent.*—'JACclam' (America).

FLOWER

Observations made cover a three year period of plants commencing at one year of age grown on their own roots in a garden environment at Somis, Calif.

Blooming habit: Continuous.
Bud:
*Size.*—About 25 mm long and 17–18 mm in diameter when the petals start to unfurl.
*Form.*—The bud form is long, pointed ovoid.
*Color.*—When sepals first divide, bud color is Orange-Red Group 34A. When half blown, the upper sides of the petals are Red Group 41B; and the lower sides of the petals are Red Group 43C.

*Sepals.*—Color: Upper surface: Green Group 138B. Lower surface: Green Group 137C. Length: 22–26 mm. Width: 9–10 mm. Shape: Subulate. Surface texture: Upper surface: Hoary. Lower surface: Coriaceous, puberulent with some glands. There are three normally appendaged sepals. There are two unappendaged sepals with hairy and glandular edges.

*Receptacle.*—Color: Green Group 137D. Shape: Funnel. Size: Medium, about 8 mm long×8 mm wide. Surface: Puberulent.

*Peduncle.*—Length: Short, averaging about 40 mm long. Surface: Puberulent. Color: Green Group 137D, sometimes with an overlay of Greyed-Red Group 178A. Strength: Stiff, erect.

Bloom:

*Size.*—Medium. Average open diameter is about 10 cm.

*Borne.*—In pyramidal clusters of 4–10 blooms.

*Stems.*—Strength: Strong. Average length is about 30–40 cm on side shoots, 120–150 cm on main shoots with a diameter of 5–6 mm on side shoots and 8–9 mm on main shoots.

*Form.*—When first open: High centered. Permanence: Flattens, all petals curl.

*Petalage.*—Number of petals under normal conditions: 20.

*Color.*—The upper sides of the petals are Red Group 41B. The reverse sides of the petals are Red Group 43C. The base of each petal has color spot 6 mm×6 mm of Yellow Group 3C. The major color on the upper side is Red Group 41B.

*Variegations.*—Occasional streak on the reverse side of the outer (guard) petals of White Group 155B.

*Discoloration.*—The general tonality at the end of the first day: No change. At the end of the third day: No change. Further aging: By day five the upper color changes to Red Group 41C. Petal drop follows. Petal reverse does not change color.

*Fragrance.*—Light and fruity.

Petals:

*Texture.*—Thick.

*Shape.*—Obcordate.

*Size.*—Length: 45 mm. Width: 40 mm.

*Surface.*—Smooth.

*Margin.*—Entire. Apex Shape: Obcordate. Base Shape: Rounded.

*Form.*—Tips slightly recurved.

*Arrangement.*—Regularly arranged.

*Petaloids.*—Number: One or two. Color: Upper portion Red Group 41B, Lower portion Red Group 43C. Shape: Subulate. Length: 3–7 mm. Width: 1–4 mm.

*Persistence.*—Petals drop off cleanly before drying.

*Lastingness.*—On the plant: Fair (about 5–6 days). As a cut flower: Fair (about 7 days).

Reproductive parts:

*Stamens.*—Number: 60–70. Length: 9–12 mm. Anthers: Length: 3 mm. Color: Yellow-Orange Group 16C. Arrangement: Regular around styles. Filaments: Color: Red Group 45C. Length: 6–9 mm. Pollen: Color: Orange Group 26C.

*Pistils.*—Number: 25–30. Length: 5 mm. Styles: Color: Red Group 53B. Length: 4 mm. Stigmas: Color: White Group N 155C. Length: 1 mm.

*Hips.*—Color: Greyed-Orange Group 171B. Shape: Spherical. Surface Texture: Smooth. Size: 25–30 mm diameter, 15–20 seeds inside hips.

*Seeds.*—Color: Yellow-Orange Group 18C. Length: 3 mm. Width: 2 mm. Configuration: Random within an enlarged hypanthium.

PLANT

*Form.*—Climber.

*Growth.*—Very vigorous.

*Age at maturity.*—3 years.

*Mature plant.*—Height: 15 feet. Width: 12 feet.

Rootstock.—Own roots.

Foliage: Number of leaflets on normal mid-stem leaves: 5–7.

*Size.*—Medium. About 14–15 cm long×10–12 cm wide.

*Quantity.*—Normal.

*Color.*—New foliage: Upper side: Greyed-Red Group 178A. Lower side: Greyed-Red Group 178A. Old foliage: Upper side: Green Group 139A. Lower side: Green Group 137C.

Leaflets:

*Size.*—Length: 40–45 mm. Width: 35–40 mm.

*Shape.*—Pointed oval.

*Base shape.*—Rounded.

*Apex shape.*—Acuminate.

*Texture.*—Leathery, glossy.

*Edge.*—Serrated.

*Serrations.*—Single.

*Petiole.*—Color: Yellow-Green Group 146D. Surface texture: Smooth.

*Petiole rachis.*—Color: Yellow-Green Group 146C. Underside: Rough with prickles and glands.

*Auricles.*—None.

*Stipules.*—Length: 20–22 mm, serrated. Shape: Adnate. Color: Green Group 146C.

*Disease resistance.*—Resistant to mildew and rust and susceptible to blackspot under normal growing conditions.

*Pest resistance.*—None observed.

*Vein color.*—Yellow-Green Group 146D.

*Venation pattern.*—Reticulate.

Wood:

*New wood.*—Color: Yellow-Green Group 146C often overlain with Greyed-Red Group 178B. Bark: Smooth.

*Old wood.*—Color: Green Group 137C. Bark: Smooth.

Prickles:

*Quantity.*—On main canes from base: Average of 8 per 10 cm. On laterals from main canes: Average of 8 per 10 cm.

*Form.*—Straight to slightly hooked downward.

*Length.*—10–12 mm.

*Color when young.*—Greyed-Red Group 178B.

*Color when mature.*—Greyed-Orange Group 175C.

Small prickles:

*Quantity.*—On main stalks: None. On laterals: None.

Winter hardiness: Hardy to Zone 5.

I claim:

1. A new and distinct variety of rose plant of the climber class, substantially as herein shown and described, characterized particularly by its strong, vigorous climbing habit; glossy, disease resistant foliage; constant bloom during the growing season; large flower clusters; good bud form; and ability to grow vigorously on its own roots.

* * * * *

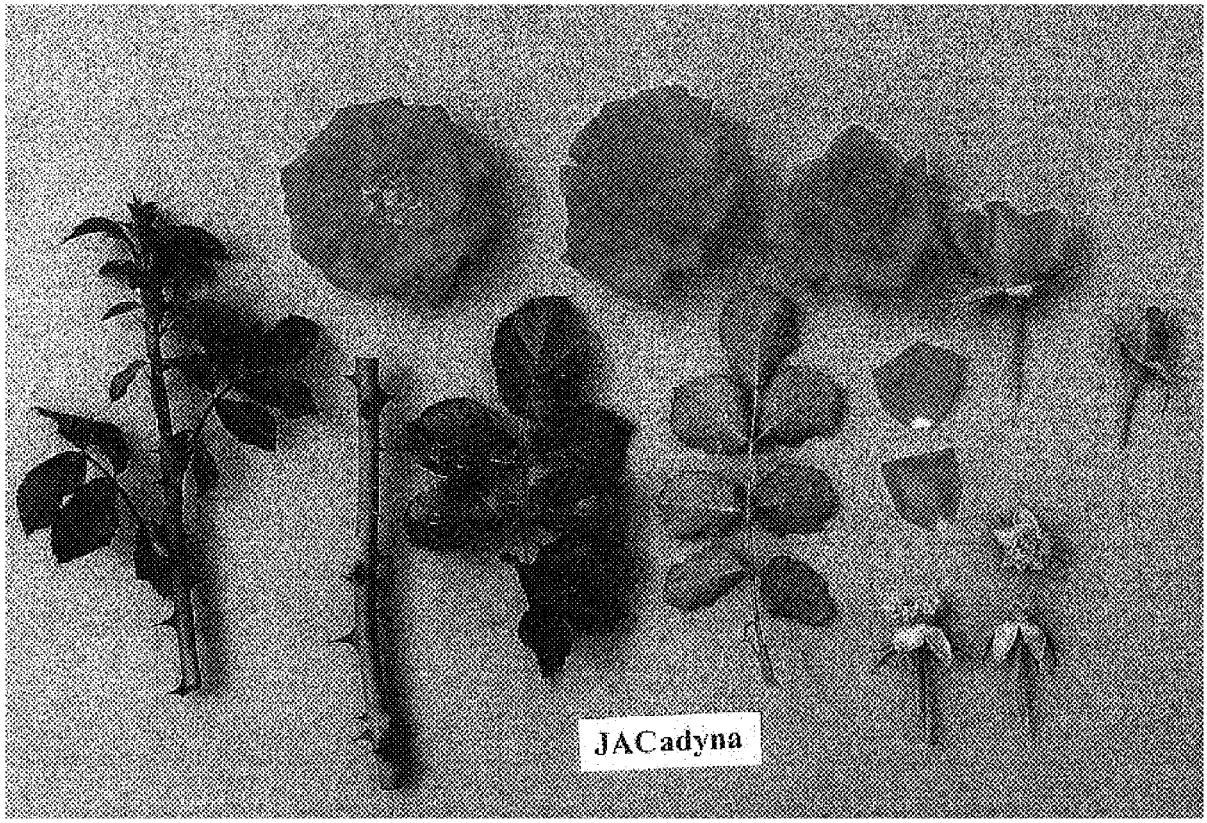
JACadyna